(12) United States Patent
Cook

(10) Patent No.: US 10,139,341 B2
(45) Date of Patent: Nov. 27, 2018

(54) SELF-CALIBRATING OPTICAL DETECTOR

(71) Applicant: TT Electronics Plc, Carrollton, TX (US)

(72) Inventor: Troy Don Cook, Dallas, TX (US)

(73) Assignee: TT ELECTRONICS PLC, Carrolloton, TX (US)

( * ) Notice: Subject to any disclaimer, the term of this patent is extended or adjusted under 35 U.S.C. 154(b) by 140 days.

(21) Appl. No.: 15/170,511

(22) Filed: Jun. 1, 2016

(65) Prior Publication Data

US 2017/0343473 A1     Nov. 30, 2017

Related U.S. Application Data

(60) Provisional application No. 62/343,657, filed on May 31, 2016.

(51) Int. Cl.
    *H01J 40/14*      (2006.01)
    *G01N 21/59*      (2006.01)
    *G01N 21/86*      (2006.01)

(52) U.S. Cl.
    CPC .............. *G01N 21/59* (2013.01); *G01N 21/86* (2013.01); *G01N 2021/8663* (2013.01); *G01N 2201/062* (2013.01); *G01N 2201/12723* (2013.01)

(58) Field of Classification Search
    CPC ................... G01N 21/59; G01N 21/86; G01N 2021/8663; G01N 2201/12723; G01N 2201/062
    USPC .............................................. 250/205, 214 R
    See application file for complete search history.

(56) References Cited

U.S. PATENT DOCUMENTS

| | | | |
|---|---|---|---|
| 4,836,682 A * | 6/1989 | Keenan, III | ............ G01S 7/497 327/514 |
| 7,509,113 B2 | 3/2009 | Knoedgen | |
| 9,681,123 B2 * | 6/2017 | Perry | ................... H04N 17/002 |
| 2007/0188337 A1 | 8/2007 | Mi et al. | |
| 2010/0085199 A1 | 4/2010 | Gonzales | |
| 2011/0181892 A1 | 7/2011 | Ritter et al. | |

* cited by examiner

*Primary Examiner* — Kevin Pyo
(74) *Attorney, Agent, or Firm* — Haynes and Boone, LLP

(57) ABSTRACT

The present disclosure includes systems and methods for calibration of an optical sensor package, including setting an initial detection threshold of a detector, gradually increasing a power level of a signal generator that is in communication with a detector to cause a detected power at the detector to exceed the initial detection threshold, storing in a memory a first power level of the signal generator at which the detected power at the detector exceeds the initial detection threshold, and adjusting the initial detection threshold of the detector to an adjusted detection threshold to include a detection buffer amount within the adjusted detection threshold.

19 Claims, 5 Drawing Sheets

SELF-CALIBRATING OPTICAL DETECTOR

CROSS-REFERENCE TO RELATED APPLICATIONS

The present application claims the benefit of U.S. Provisional Patent Application No. 62/343,657 filed May 31, 2016, and entitled "Self-Calibrating Optical Detector," the disclosure of which is incorporated by reference herein in its entirety.

TECHNICAL FIELD

The present description relates, in general, to systems and techniques for self-calibrating optical sensor packages used to detect changes in a target medium.

BACKGROUND

In various industries there is a need for sensor packages that are able to detect changes in materials passing between a signal generator and a detector at a high rate of speed. For example, a user may wish to count a number of adhesive labels affixed to a strip of backing paper while running a sheet of backing paper with adhesive labels affixed to one side through a sensor package. By sensing the change in transparency between the label and the backing paper, the sensor package may detect each label as it passes between the signal generator (e.g., a light emitting diode) and the detector (e.g., a photodectector).

The change that the sensor package is looking for may be extremely small, requiring very sensitive detection. In some applications, this change may be small enough that variances in manufacture of parts of the sensor package, variances in temperature of the sensor package, variations in the path of the materials as they pass through the sensor package, etc. could result in errors in detection. It is therefore necessary to calibrate the sensor package to the particular environment it is being used in and with the particular components that the sensor package has been assembled from. Typically, this calibration is done manually and one time permanent adjustments are made to the sensor package based on testing in the target environment. It is therefore desirable to improve upon this method of calibration.

SUMMARY

It is therefore desirable to have systems and methods that allow self-calibration of sensor packages by setting a detection threshold for a detector, ramping up the power level of a signal generator so that the detector receives signal energy that exceeds the detection threshold under normal operating conditions, and adding a detection buffer amount into the detection threshold to ensure that detection will occur even with variances in the system that reduce the signal energy received at the detector.

In one aspect of the disclosure, a method of calibration includes setting, by a controller, an initial detection threshold of a detector. The method further includes gradually increasing a power level of a signal generator, the signal generator being in communication with the detector and the controller, causing a detected power at the detector to exceed the initial detection threshold. The method further includes storing in a memory, by the controller, a first power level of the signal generator at which the detected power at the detector exceeds the initial detection threshold. The method further includes adjusting, by the controller after the power level of the signal generator reaches the first power level, the initial detection threshold of the detector to an adjusted detection threshold to include a detection buffer amount within the adjusted detection threshold.

In another aspect of the disclosure, a computer program product has a computer readable medium tangibly recording computer program logic for calibrating a detector and a signal generator. The computer program product includes code to receive, from a user, a detection threshold setting signal including the initial detection threshold. The computer program product further includes code to receive, from the user, a calibration signal instructing the computer program product to begin gradually increasing the power level of the signal generator. The computer program product further includes code to receive, from the user, a threshold change signal including the user-programmable amount to adjust the initial detection threshold by.

In yet another aspect of the disclosure, a computing device includes a memory containing machine readable medium comprising machine executable code having stored thereon instructions for performing a method of calibrating a sensor and a signal generator. The computing device further includes a processor coupled to the memory, the processor configured to execute the machine executable code to cause the processor to set an initial detection threshold of the sensor. The processor is further configured to execute the machine executable code to gradually increase a power level of the signal generator, the signal generator being in communication with the sensor, causing a detected power at the sensor to exceed the initial detection threshold. The processor is further configured to execute the machine executable code to store in a memory a first power level of the signal generator at which the detected power at the sensor exceeds the initial detection threshold. The processor is further configured to execute the machine executable code to adjust the initial detection threshold, after the signal generator reaches the first power level, of the sensor to an adjusted detection threshold to include a detection buffer amount within the adjusted detection threshold.

DETAILED DESCRIPTION

Figure 1A:
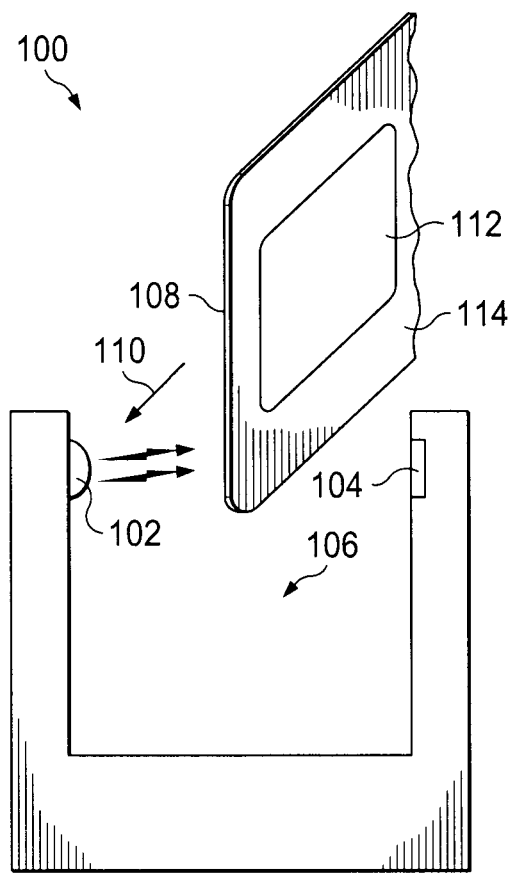
FIG. 1A is an illustration of an optical sensor package according to an embodiment of the present disclosure.

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. However, it will be apparent to those skilled in the art that these concepts may be practiced without these specific details.

The present disclosure describes systems and methods for self-calibration of a sensor system including a signal generator and a detector in order to detect changes in a target medium. For simplicity, the embodiments described herein will use an optical sensor package using a light emitting diode (LED) as the signal generator and a photodiode as the detector, although the scope of embodiments may include any appropriate signal generator or photon detector.

In certain applications, the sensor package may be used to detect small changes in light received at the photodiode. For example, the difference in transparency (or transmittance) between a label affixed to a backing paper and the backing paper itself may be very small. The sensor package should be able to sense this slight change in transparency. However, the change may be so small that variations in manufacturing of the sensor package and variations in the environment may cause false detections. For example, variations in the LED output or photodiode sensitivity, variations in the lens of the LED package or the photodiode package, variations in the placement of the LED or photodiode within the sensor package, variations in temperature in the sensor package, variations in the path of the target medium through the sensor package, etc. may each alone or in combination be enough to cause detection errors.

In order to prevent detection errors due to these variations, it is desirable to calibrate the sensor package. In an exemplary embodiment, the sensor package is designed to self-calibrate. Self-calibration may be initiated by a command from a user, or may be automatic upon powering on the sensor package. In some embodiments a user may supply various parameters to the sensor package before calibration, as will be further described below.

Embodiments of the present disclosure describe systems and methods for calibrating an optical sensor package to detect a change between two target materials as they pass by the sensor. Upon receiving a calibration request, the output power of an LED is ramped up until light from the LED that is received at a photodiode exceeds a pre-set detection threshold. The LED power level at which detection occurred is then saved as a calibration parameter. When operating the sensor package using the above detection threshold and LED power level to sense target materials, however, variations in the system which lower the amount of light received at the photodiode even a small amount will lower the received light below the detection threshold, resulting in a failure to detect when desired.

To solve this problem, a detection buffer amount is provided by adjusting the detection threshold by an amount that exceeds expected variations. For example, if variations might reduce the amount of light received at the photodiode by up to 15%, then lowering the detection threshold by 20% ensures that variations will not cause the received light level to drop below the detection threshold. In this example, the detection buffer amount is the 5% difference between the adjusted detection threshold and the expected effects of variation on the detector.

Of course, the percentages given above are examples, as other systems may include different detection buffer amounts as appropriate. In various embodiments, an appropriate detection buffer amount may be calculated or acquired through testing, simulation, or other means, allowing the detection threshold to be adjusted so that the difference between the effects of variation and the adjusted detection threshold reduces the chances of false detection to a level that is acceptable for a particular application. The adjusted detection threshold is saved as a calibration parameter. When the optical sensor package is powered on, for example after a loss of power, the LED power level and adjusted detection threshold are applied so that re-calibration is not necessary.

One embodiment of the disclosure includes a controller that has memory addresses for storing calibrated values and for storing computer-readable code to use those calibrated values during normal detection operation. In one example, a user begins a calibration operation by setting a first threshold for detection in a memory address in the controller. The system then verifies the first threshold by ramping up an amplifier level of a signal generator until the detector detects the signal reaching the first threshold. If the detector does not detect the signal using the first threshold, then the user may change the first threshold so that the signal may be detected with an operating range of the signal generator based on its available amplifier levels.

The calibration operation continues, assuming that the first threshold level has been verified with a successful detection, by the controller storing the amplifier level corresponding to a point where the first threshold level is reached. The user may then adjust the detection level by setting a second detection threshold having a detection buffer amount therein. The detection buffer is explained in further detail below, and in this embodiment it corresponds to an amount representing a difference between effects of expected variation and the second threshold level so that false detections and/or lack of detections are avoided. The controller then stores the amplifier level and the second threshold in memory addresses that are used during normal operation of the controller. Upon reboot or at some other appropriate later time, the controller then uses the amplifier level and the second threshold to perform detection, and the detection buffer amount built into the second threshold should reduce or minimize undesirable operation that would otherwise be caused by variation.

Referring now to FIG. 1A, there is illustrated an optical sensor package 100 according to an embodiment of the present disclosure. In this embodiment, the sensor package 100 includes an LED 102 and a photodiode 104, with a slot 106 between them, through which a target medium 108 may be passed as indicated by the directional arrow 110. In some embodiments, the LED 102 may be an infrared (IR) LED or other appropriate wavelength. The LED 102 outputs light directed towards photodiode 104. As the target medium 108 passes through the slot 106, the amount of light transmitted through the target medium 108 changes depending upon the transmittance of the portion of the target medium 108 that is between LED 102 and photodiode 104. In some embodiments, a first portion 112 of target medium 108 may be more opaque or more reflective than a second portion 114 of the target medium 108. For example, the target medium 108 may be a strip of backing paper with adhesive labels attached to it. In this example, the labels are a first portion 112 of the target medium 108 that is more opaque than the backing paper, which is a second portion 114 of the target medium 108.

Figure 1B:
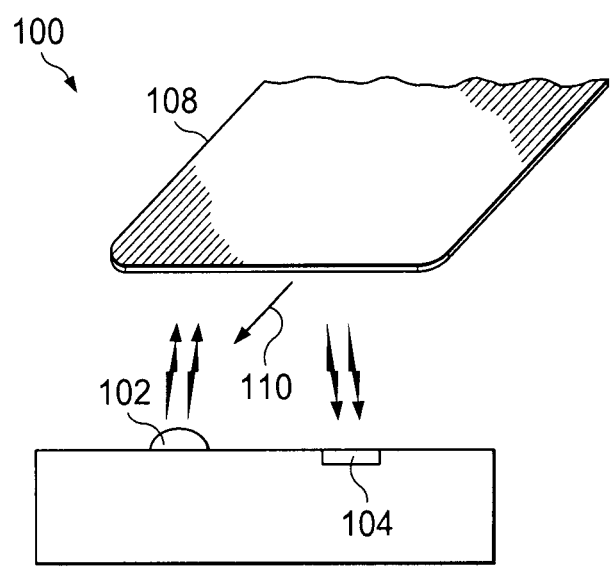
FIG. 1B is an illustration of an alternative optical sensor package according to an embodiment of the present disclosure.

Referring now to FIG. 1B, there is illustrated an alternative embodiment of an optical sensor package 100 according to an embodiment of the present disclosure. In this embodiment, an LED 102 and photodiode 104 are positioned near each other and a target medium 108 is passed over both the LED 102 and photodiode 104, as indicated by the directional arrow 110. In this embodiment, the LED 102 outputs light directed towards the target medium 108, and the photodiode 104 detects light reflected off of the target medium 108. As the target medium 108 passes over the sensor package 100 along directional arrow 110, the amount of light reflected off of the target medium 108 changes depending upon the reflectance of the portion of the target medium 108 that is between LED 102 and photodiode 104.

Figure 2:
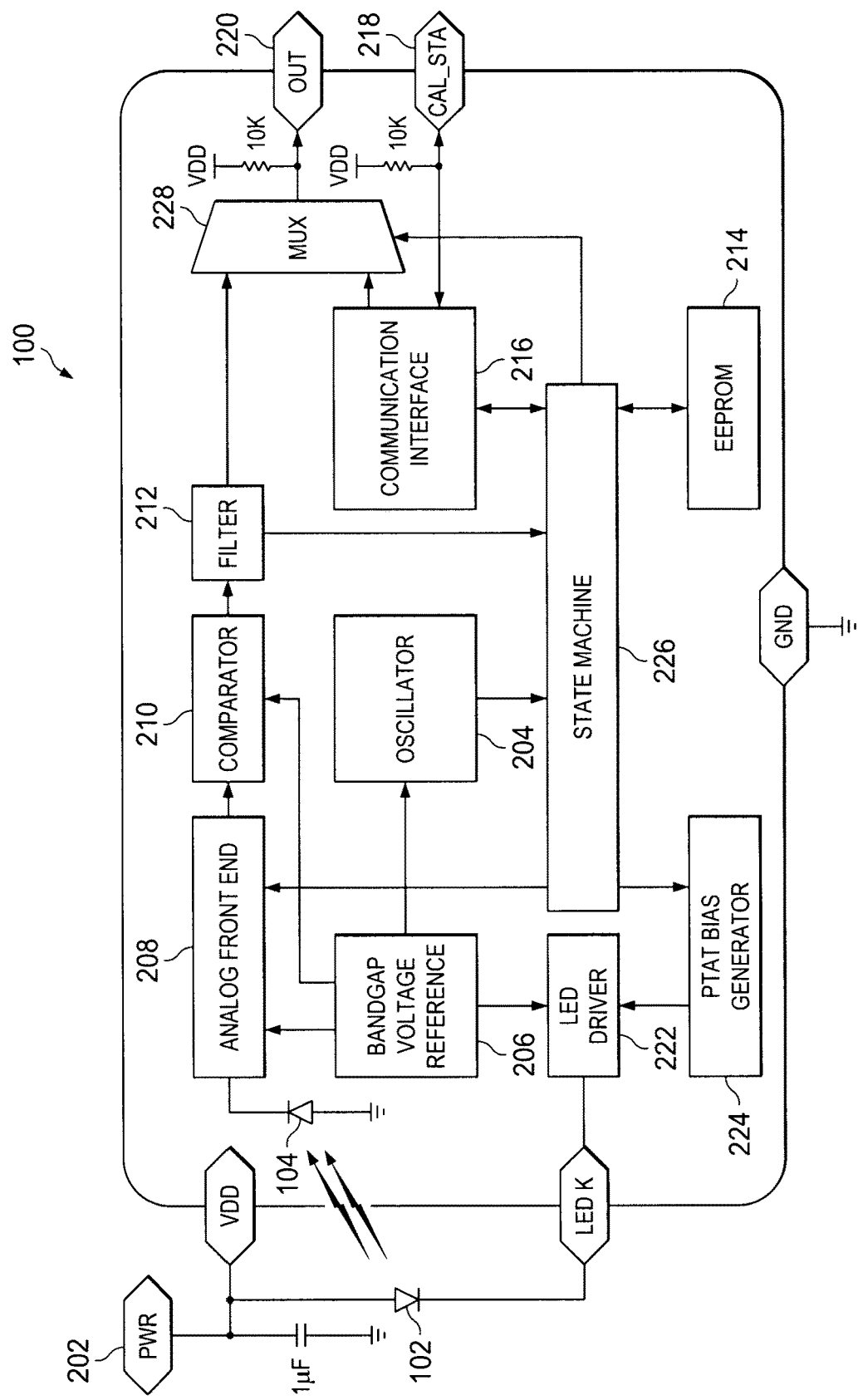
FIG. 2 is an illustration of a control system of the optical sensor package according to an embodiment of the present disclosure.

Referring now to FIG. 2, there is illustrated a control system of the optical sensor package 100 according to an embodiment of the present disclosure. The control system of FIG. 2 may be implemented as an Application Specific Integrated Circuit (ASIC) executing logic to perform the actions indicated in the state machine of FIG. 3. However, the scope of embodiments may include any kind of logic circuit, such as a general-purpose central processing unit, executing machine-readable code to perform the calibration and detection actions described herein. A power supply 202 provides power to the circuit. An oscillator 204 produces a clock signal to provide timing for operation of the circuit of the sensor package 100. In some embodiments, the oscillator 204 may provide a high frequency clock signal, for example a 4 MHz signal. A bandgap voltage reference 206 produces a fixed voltage independent of the voltage supplied by power supply 202 and independent of temperature variations in the system. This fixed voltage is fed to other elements of the system that benefit from a fixed voltage, for example the oscillator 204, the analog front end 208, the comparator 210, and the LED driver 222.

Analog front end 208 receives analog signals from the LED 102 and processes them for comparison to a user-determined detection threshold at comparator 210, as will be further described below. In some embodiments, the photodiode 104 is part of the analog front end 208, although it is understood that the photodiode 104 may be a discrete element attached to the analog front end 208. Analog front end 208 further includes a trans-impedance amplifier, an integrator stage, a gain stage, and a comparator with programmable reference generator. The trans-impedance amplifier serves to amplify the output of the photodiode 104 to a voltage usable by the rest of the system.

The trans-impedance amplifier of analog front end 208 may have its own gain controlled by a bandpass filtered feedback loop to compensate for current generated by the photodiode 104 in response to ambient light. The gain of the trans-impedance amplifier may be further controlled by an automatic gain selection circuit that automatically increases the gain of the trans-impedance amplifier during calibration depending on the strength of the signal received by photodiode 104 from LED 102, as will be further described below with reference to FIG. 4. The automatic gain selection circuit may also be provided with a gain level to use by the state machine 226 if calibration has already occurred. In some embodiments, the automatic gain selection circuit may have 3 gain settings although any appropriate number of games settings may be used in some embodiments.

The integrator stage of analog front end 208 performs various functions, such as removing low frequency noise and power supply ripple, referencing the photodiode 104 signal to the bandgap reference voltage 206, and generating a saw-tooth signal from the output (which may be a pulse) of the photodiode 104, thereby decreasing the effect of bandwidth variations in the output of the photodiode 104. The gain stage of the analog front end 208 boosts the output signal to a level that is useful at the comparator 210.

Comparator 210 receives the output of the analog front end 208 and a pre-programmed reference level, and compares the two. The output state of the comparator 210 changes based on this comparison. For example, when the output of the analog front end 208 exceeds the pre-programmed reference level, the output state may be a binary one or may be a binary zero when the output of the analog front end 208 is below the reference level (or vice versa). In other words, the output state may change as the output level of the front end 208 changes to either be above or below the reference level. The reference level may therefore serve as a detection threshold. In an embodiment, the pre-programmed reference level may be chosen by a user from a range of 16 available reference levels (e.g., each reference level is about a 7% change from the next reference level), although the scope of embodiments includes any appropriate number of available reference levels.

The output of comparator 210 is passed to a filter 212. The filter 212 serves to filter out changes in state of the comparator 210 that result from events other than detection of the desired portion of the target medium 108. Such events may include ambient light incident on the photodiode 104 that causes the analog front end 208 output to exceed the reference level at the comparator 210, electrical noise in the sensor package 100 that causes the comparator 210 to output a state change, or the like. The filter 212 may require a state change to be seen at its input for multiple consecutive cycles before it passes the state change to its output. In some embodiments, the filter 212 may wait until the input is held at a changed state for an appropriate amount of clock cycles (e.g., 2 cycles) before outputting the state change. The state change may be output to state machine 226 and to multiplexer 228, both discussed further below.

Memory 214 stores various pieces of information used by the sensor package 100. In the present embodiment, memory 214 is an Electronically Erasable Programmable Read Only Memory (EEPROM), but may be any other suitable memory device. In one example, memory 214 stores computer-readable code to be read and executed by the processor providing the logic of state machine 226. In some embodiments, various pieces of information related to calibration of the sensor package 100 are stored in the memory 214 after calibration is performed, and the memory 214 is accessed by the state machine 226, as described below with reference to FIGS. 3 and 6, to retrieve the calibration information upon powering up the sensor package 100. For example, the memory 214 may store a drive level for the LED driver 222, an automatic gain selection value for the trans-impedance amplifier gain of the analog front end 208, a calibration bit (or flag) indicating whether the sensor package 100 has been previously calibrated, an output type and polarity, a detection threshold for the comparator 210, an internal oscillator calibration factor for the oscillator 204, and a temperature compensation factor for the bias generator 224.

Communication interface 216 facilitates communication between the sensor package 100 and the user for functions such as calibration. The communication interface 216 may, for example, be an interface to an I2C bus. An external microcontroller that is controlled by the user may connect to the sensor package 100 via calibration status pin 218 and output pin 220. In an embodiment, inputs to the communication interface 216 are received via the calibration status pin 218 and passed to the state machine 226, which is further described below. Outputs are received from the state machine 226 and sent to the user microcontroller via either the calibration status pin 218 or the output pin 220, depending on the type of output. Outputs of the communication interface 216 sent to the output pin 220 may be multiplexed with the output of comparator 210 by multiplexer 228, as will be further described below.

LED driver 222 drives the LED 102 based on input received from the state machine 226, which is further described below. The LED driver 222 may, in some embodiments, drive the LED 102 up to 95 mA at room temperature, although any appropriate maximum or minimum current may be used in some embodiments. As will be further described below, the LED driver 222 may be controlled by outputs from the state machine 226.

Bias generator 224 may be a Proportional To Absolute Temperature (PTAT) bias generator that provides a current to the LED driver 222 based on the internal temperature of the sensor package 100. The current supplied to the LED driver 222 may cause the output of the LED driver 222 to scale in magnitude as the internal temperature of the sensor package 100 changes. This may, for example, compensate for variance in the LED 102 output due to changes in temperature.

State machine 226 manages the functions of various parts of the sensor package 100 automatically during power up and dynamically based on user inputs received via the calibration status pin 218. In the present embodiment, the state machine 226 manages the function of various elements including the memory 214, the communication interface 216, the LED driver 222, and the multiplexer 228. State machine 226 represents the logic functions of the ASIC or other processor as it performs the calibration process is described herein. Although a processor is not explicitly shown as a hardware portion in FIG. 2, it is understood that the system of FIG. 2 may be embodied as an ASIC or other processor, including the inputs, outputs, and power terminals.

The multiplexer 228 receives inputs from the filter 212 and the communications interface 216, and multiplexes them to output pin 220. State machine 226 provides the selector input to multiplexer 228, thereby selecting which of the inputs are passed through multiplexer 228 to the output pin 220. Normally, the output of filter 212 will be selected for output. This allows the user to read the processed output of the photodiode 104 to determine whether or not a target medium has been detected. In some embodiments, the user controller may send a read request to the state machine 226 (e.g., for calibration information from memory 214), in which case the state machine 226 will retrieve the requested information from memory 214 and pass it through the communications interface 216 to the multiplexer 228, then select the input from the communication interface for output from the multiplexer to output pin 220.

Figure 3:
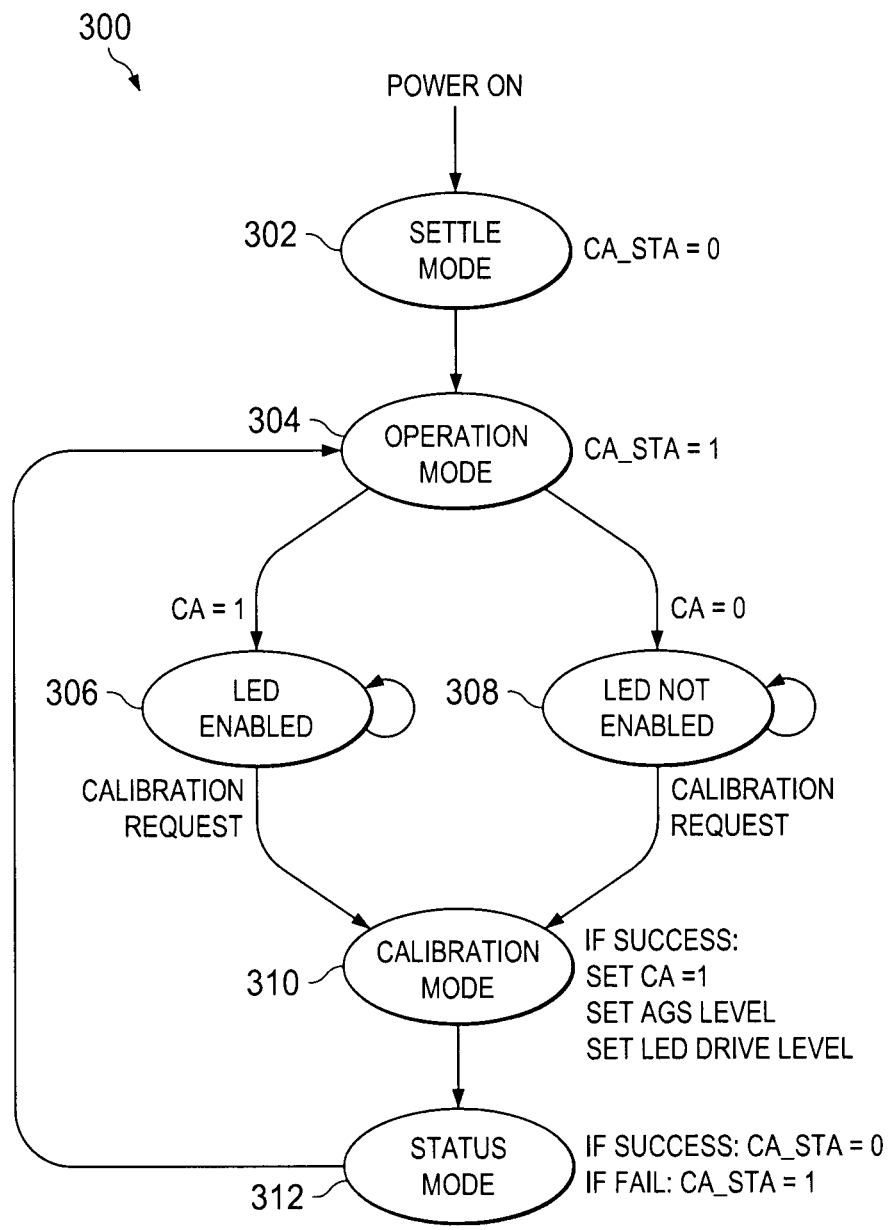
FIG. 3 is an illustration of a state diagram for the operation of a state machine according to an embodiment of the present disclosure.

Referring now to FIG. 3, there is illustrated a state diagram 300 for the operation of state machine 226 according to an embodiment of the present disclosure. Upon powering on the sensor package 100, the state machine 226 enters settle mode 302 for a period of time that allows the memory 214 to settle to a stable state. This period may be from about 2.5 mS to about 26 mS for an EEPROM memory 214, depending on the frequency of oscillator 204. However, it is understood that any appropriate duration for the settle mode 302 may be used in various embodiments. In settle mode 302, the calibration status pin 218 becomes an output from the state machine 226, and is set to a state that indicates to the user microcontroller that the sensor package 100 is in settle mode 302. In some embodiments, the calibration status pin 218 may be set to a low binary state (logical "0") for this purpose. After allowing the maximum possible amount of time for the memory 214 to settle, the state machine 226 may retrieve from the memory 214 the automatic gain selection, which is provided to the trans-impedance amplifier of the analog front end 208 to adjust the gain setting. In some embodiments, there may be any appropriate number of potential gain settings, and 2 or more bits in memory 214 may contain the automatic gain selection value. Retrieval of the automatic gain selection value may take from 10 microseconds to 102 microseconds, although in operation various embodiments may use any appropriate amount time.

After the settling period has ended and the automatic gain selection value has been retrieved, the state may automatically transition to operation mode 304. During operation mode 304, the calibration status pin 218 becomes an input to the state machine 226 and the communication interface 216 is enabled to receive communications from the user. In some embodiments, calibration status pin 218 may be pulled high (to logical "1") by an internal pull-up resistor while in operation mode 304. The state machine 226 then reads from memory 214 a calibration flag which indicates whether or not previous calibration has occurred.

If the calibration flag is set (e.g., a flag bit is set to "true" or logical "1"), then the state machine 226 transitions to LED driver enabled mode 306. The state machine 226 reads from memory 214 a calibrated LED driver level and enables the LED driver 222 to begin sending pulses at the calibrated level.

If the calibration flag is not set (e.g., the flag bit is set to "false" or logical "0"), then the state machine 226 transitions to LED driver not enabled mode 308. In this state the LED driver 222 is disabled, and the state machine 226 simply waits for a calibration request from the user.

When a calibration request is received via the calibration status pin 218 from the user (e.g., from the user controlled microcontroller) in either LED driver enabled mode 306 or LED driver not enabled mode 308, the state machine 226 transitions to calibration mode 310. When calibration mode 310 is entered, the state machine 226 lets the calibration status pin 218 return to being pulled up to high. Furthermore, the state machine 226 directs the memory 214 to clear the calibration-related values (e.g., the LED drive level, automatic gain selection value, and the calibration flag), and allows time for the memory 214 to settle (e.g., about 5 mS).

The state machine 226 directs the calibration process, further described below with reference to FIG. 4. After successful calibration, the state machine 226 directs the memory 214 to store various calibration values. For example, the memory 214 may store the LED drive level resulting from the calibration, the automatic gain selection value used for successful calibration, and it may set the calibration flag to indicate successful calibration (e.g., to "true" or logical "1"). If calibration is not successful, the state machine 226 may leave memory 214 unchanged.

After calibration has finished, whether successful or not, the state machine 226 may transition into status mode 312. Calibration takes a known amount of time. In the method of FIG. 4, for example, calibration may take about 10 mS. After the memory settling time and the calibration time have elapsed, which may take about 15 mS total, the user controller may be programmed to look for a calibration complete signal during a selected window of time. If calibration has completed successfully, the state machine 226 may drive the calibration status pin 218 low (e.g., logical "0") during the selected window to indicate to the user that calibration was successful. If calibration was not successful, the state machine 226 may leave the calibration status pin 218 high (e.g., logical "1") during the selected window. After the selected window has elapsed, the state machine 226 automatically transitions back to operation mode 304 until further user input, such as another calibration request, is received.

Figure 4:
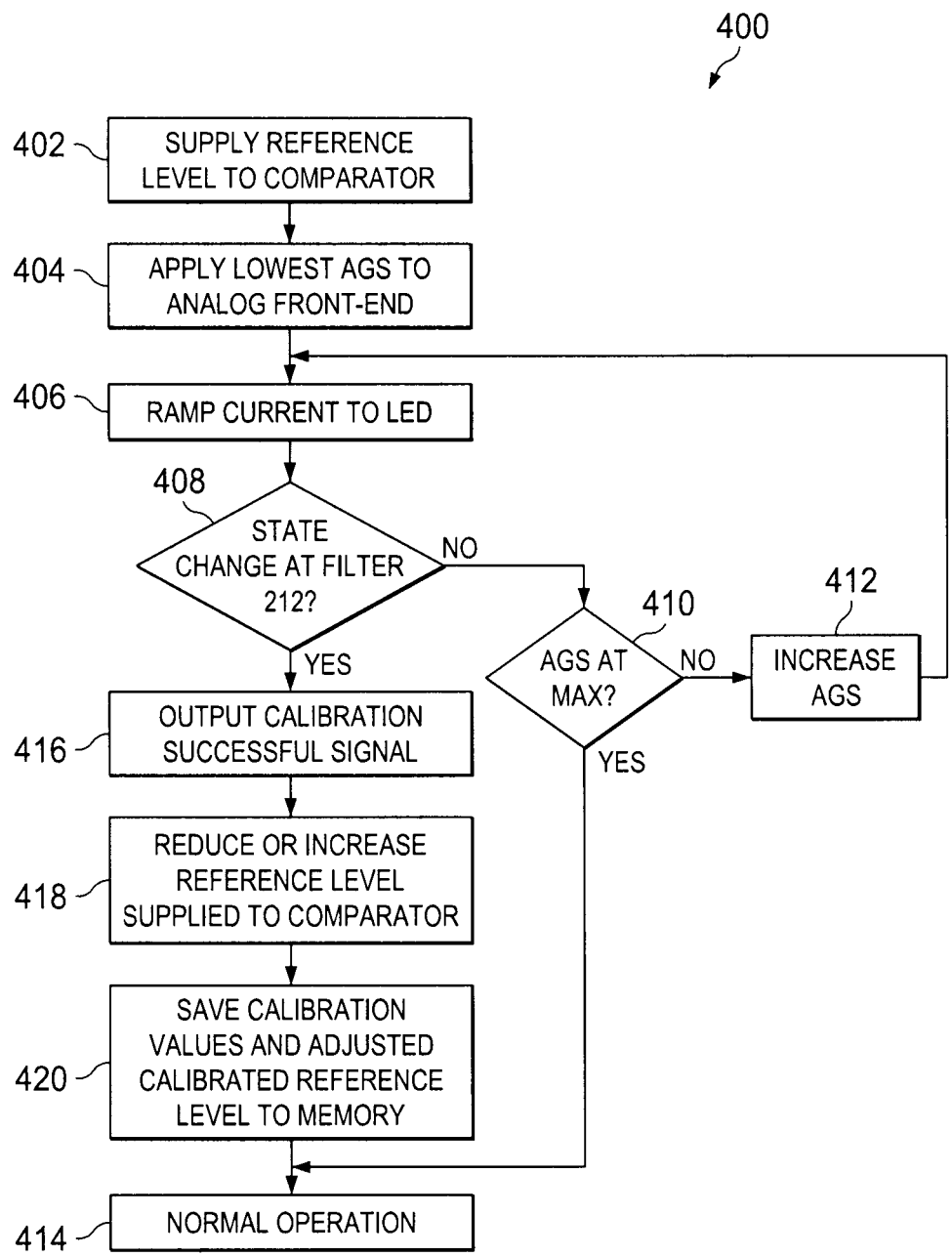
FIG. 4 is an illustration of a block diagram of a method for self-calibration of the sensor package according to an embodiment of the present disclosure.

Referring now to FIG. 4, there is illustrated a block diagram of a method 400 for self-calibration of the sensor package 100 according to an embodiment of the present disclosure. For ease of illustration, reference will be made to an embodiment where the sensor package 100 is designed to detect a decrease in light received at the photodetector 104 (i.e., to detect when the transmittance of target medium 108 increases). In this embodiment, calibration is performed with the most transmissive portion of the target medium 108 in slot 106. It is understood that calibration may also be performed with the least transmissive portion of the target medium 108 in slot 106. It is also understood that other embodiments may use a similar method to detect an increase in light received at the photodetector (i.e., to detect when the transmittance of target medium 108 increases).

At block 402, a controller, such as the state machine 226, supplies a reference level to comparator 210. As described above, the reference level may be pre-programmed by a user from a set of available reference levels. In an embodiment described above, the device may have 16 reference levels to choose from. For example, a user may direct the state machine 226 to set the reference level to 7, and the state machine may supply an appropriately scaled voltage signal to comparator 210.

At block 404, the state machine 226 applies an automatic gain selection to the trans-impedance amplifier of analog front end 208. In this example, there are 3 possible levels of gain to choose from for the automatic gain selection, and the state machine 226 begins calibration at the lowest gain selection. The automatic gain selection serves to adjust the sensitivity of the analog front end 208 to light received at the photodiode 104. The higher the gain, the more sensitive the front end 208 is to outputs from the photodiode 104.

At block 406, the state machine 226 directs the LED driver 222 to ramp up current supplied to LED 102 from a beginning current output, such as 0 mA, to a maximum current output, such as 95 mA. In some embodiments, the LED driver 222 may be instructed to send current pulses to the LED 102 while increasing current output in discrete steps, and to repeat the pulse at each current step a pre-programmed number of times. For example, the LED driver 222 may be instructed to ramp the current output from 0 mA to 95 mA in 1000 steps, or levels, (therefore increasing the current output by 95 microamps with each step), and to send the current pulse to the LED 102 at each current step 5 times. The width of each pulse may also be pre-programmed, and may be for example 250 nS. There may be a dead period, for example 150 nS, between each pulse, resulting in a period of 2 microseconds for each current step and an overall period of 2 mS to ramp through all 1000 steps. However, the number of steps, the amount of current, and the width of pulses may be different in other embodiments.

At decision block 408, the state machine 226 monitors the output of filter 212 for a change in state of the output while the LED driver 222 ramps up its current output to LED 102. As noted above, the reference level supplied to comparator 210 effectively serves as a detection threshold, and the filter 212 functions to filter out anomalous detection of values exceeding the detection threshold due to interference. Therefore, a state change in the output of filter 212 indicates a successful detection of light exceeding the detection threshold of photodiode 104 as processed by analog front end 208. If the LED driver 222 ramps all the way to its maximum current output and there is no successful detection, then the method 400 moves to decision block 410. If there is a successful detection, the method 400 moves to block 416. Each will be addressed in turn below.

At decision block 410, the state machine 226 checks whether the automatic gain selection is at its maximum value. If the automatic gain selection is not at its maximum value, the method 400 moves to block 412. If the automatic gain selection is already at its maximum value, for example it is at 3 out of 3 possible levels, then calibration has failed, and the method 400 moves to block 414. Each will be addressed in turn below.

At block 412, the state machine 226 increases the automatic gain selection at the trans-impedance amplifier of analog front end 208 in order to increase the sensitivity of the analog front end 208. For example, if the automatic gain selection is set to 1, the state machine 226 will increase it to 2. The method 400 then returns to block 406 and ramps the current of the LED driver 222 again with the new automatic gain selection applied to the analog front end 208.

Returning to decision block 410, if the automatic gain selection is at its maximum value, then the method moves to block 414.

At block 414, the state machine 226 returns the system to normal operation mode 304 as described above with reference to FIG. 3, and waits for further user input such as another calibration request.

Returning to decision block 408, if there is a successful detection, the method 400 moves to block 416.

At block 416, the state machine 226 outputs a calibration successful signal.

At block 418, upon successful detection, the state machine 226 reduces the reference level at the comparator (or increases the reference level, for example when calibration is performed with the least transmissive portion of target medium 108 in slot 106) by a pre-programmed amount to produce an adjusted calibrated reference level, and to accordingly introduce a detection buffer amount in the adjusted calibrated reference level. In some embodiments, this pre-programmed amount may be supplied by a user before calibration, and it may be around 10% to 25% of the total amount of reference levels. For example, the user may instruct the state machine to reduce the reference level by 2 out of a total 16 reference levels upon successful detection. The adjusted calibrated reference level reduces the detection threshold to create a detection buffer amount. Reducing the detection threshold introduces robustness against missed detections due to variations in the system such as internal temperature changes, changes in the path of the target medium 108 through the slot 106, dust buildup on the optical component surfaces, etc. as described below with reference to FIGS. 5A and 5B.

At block 420, the state machine 226 saves values resulting from the successful calibration into memory 214 for future use when powering on the sensor package 100. Stored values may include, for example, the LED drive level (e.g., level/step 650 out of 1000 possible power levels/steps) where successful detection occurred, the automatic gain selection at which successful detection occurred (e.g., 2 out of 3 possible automatic gain selection levels), the adjusted calibrated reference level (e.g., 7 out of 16 possible reference levels), and a "true" flag that indicates the system has been calibrated successfully.

In one example embodiment, the LED drive level is selected from 1000 possible current levels and uses 10 bits of memory 214 to store, the automatic gain selection may be selected from 3 possible levels and requires 2 bits to store, the adjusted calibrated reference level is selected from 16 possible levels and requires 5 bits to store, and the calibration flag is selected from two possible values and requires 1 bit to store. After successful calibration and storing calibration values in memory 214, the method 400 may move to block 414, which is described above, resuming normal operation mode 304.

Figure 5A:
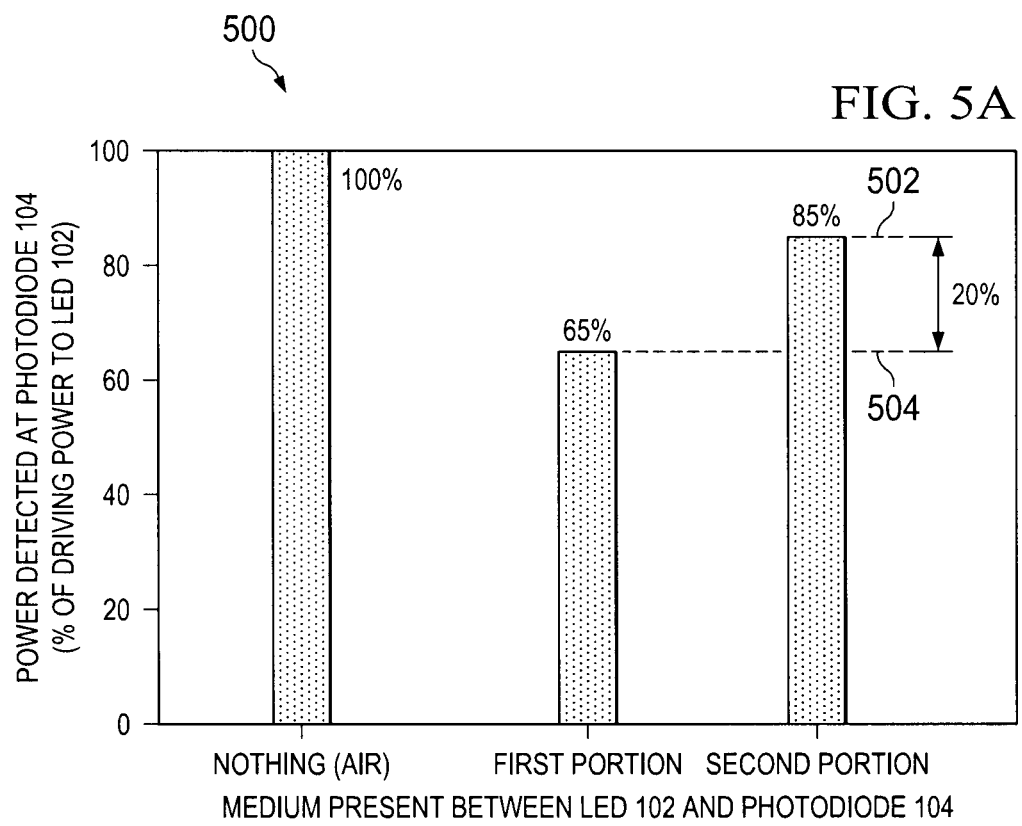
FIG. 5A is an illustration of a graph of power received at a photodiode at room temperature.

Referring now to FIG. 5A, there is illustrated a graph 500 of the power received at photodiode 104 as a percentage of power driven to LED 102. In this example, self-calibration with method 400 of FIG. 4 with the more transmissive second portion 114 in slot 106 has resulted in the non-adjusted calibrated detection threshold 502 set such that 85% of the power driven to LED 102 is received at photodiode 104 when the second portion 114 of target medium 108 is between LED 102 and photodiode 104. Incidentally, when first portion 112 of target medium 108 is between LED 102 and photodiode 104, 65% of the power driven to LED 102 is received at photodiode 104. Therefore, if the detection threshold were set to minimum detection threshold 504, the sensor package 100 would register a successful detection when either first portion 112 or second portion 114 of target medium 108 is between LED 102 and photodiode 104, which is an undesirable result. Accordingly, the adjusted calibrated reference level of block 416 of method 400 should be kept high enough to keep a detection threshold higher than minimum detection threshold 504.

Figure 5B:
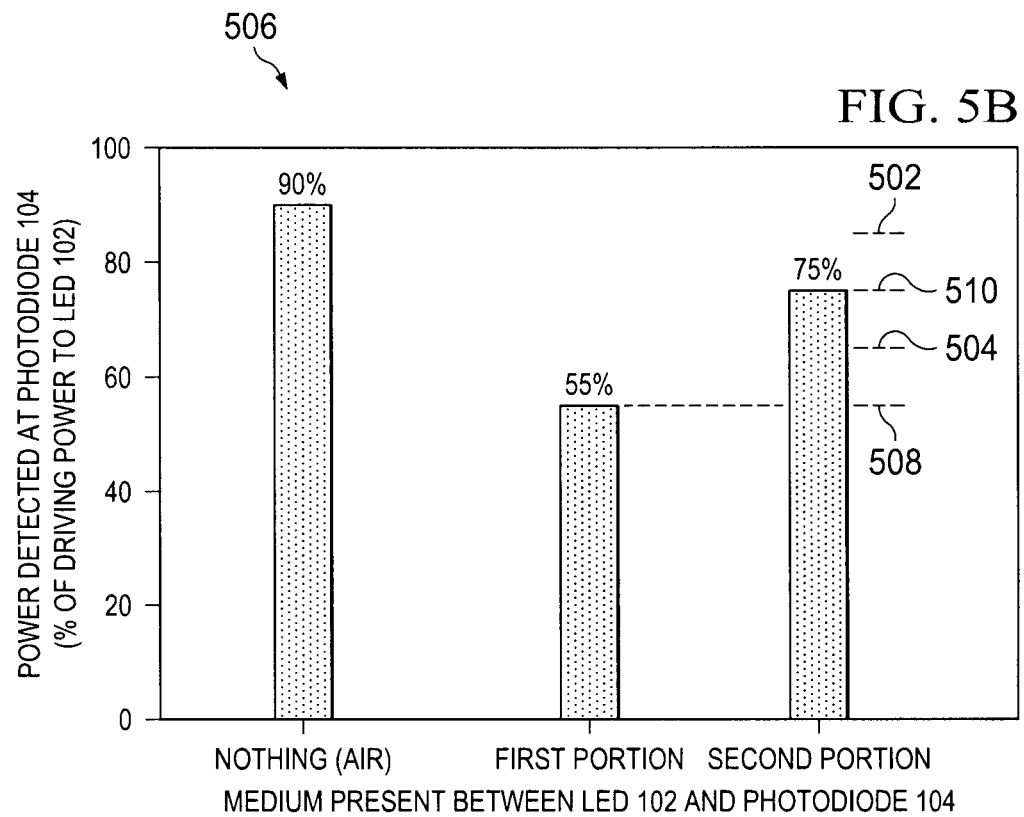
FIG. 5B is an illustration of a graph of power received at a photodiode at elevated temperature.

Referring now to FIG. 5B, there is illustrated a graph 506 of the power received at photodiode 104 as a percentage of power driven to LED 102 after dust has accumulated on a lens of the LED 102. In this example, the debris on the lens causes the LED 102 to output 10% less power as compared to operation with no dust on the lens at the same driving current. Accordingly, the power received at photodiode 104 is reduced by about 10% as well. As a result, if the calibrated reference level is not adjusted (i.e., if the detection threshold remains 502), the sensor package 100 will be unable to detect the presence of the second portion 114 of target medium 108 as the power received at photodiode 104 will not exceed detection threshold 502.

The reference level can be lowered such that the detection threshold is set to detection threshold 508, in which case the sensor package 100 will be able to successfully detect the second portion 114 of target medium 108 while discriminating from first portion 112 of target medium 108. However, as this detection threshold 508 would be lower than minimum detection threshold 504, it would result in undesirable detections of first portion 112 (i.e., first portion 112 would be detected when the sensor package 100 thinks it is detecting second portion 114) if the debris is removed from the lens of LED 102.

Alternatively, the reference level can be lowered such that the detection threshold is set to adjusted calibrated detection threshold 510, in which case the sensor package 100 will be able to successfully detect the second portion 114 of target medium 108 while discriminating from first portion 112 of target medium 108 whether dust has accumulated on the lens of LED 102 or not. In other words, sensor package 100 would register successful detections over calibrated detection threshold 510 when second portion 114 of target medium 108 is present between LED 102 and photodiode 104 at a range of obfuscation of the lens of LED 102, while not registering successful detections over calibrated detection threshold 510 when first portion 112 of target medium 108 is present between LED 102 and photodiode 104 regardless of lens obfuscation.

Accordingly, a user may test the transmittance of target medium 108 to determine the difference between first portion 112 and second portion 114, and may use the information gained to select the amount of reduction in reference level to be applied at block 416 of method 400 to obtain an appropriate adjusted calibrated reference level. For example, as shown in FIGS. 5A and 5B, if there is a 20% decrease in the amount of light detected at photodiode 104 when the first portion 112 is between LED 102 and photodiode 104 as compared to when the second portion 114 is between LED 102 and photodiode 104, then reducing the reference level by more than 20% would result in the light detected at the photodiode 104 always exceeding the detection threshold regardless of which portion of target medium 108 is between LED 102 and photodiode 104, as described above with reference to FIG. 5B.

It is understood that in some embodiments, the first portion 112 of target medium 108 may be more transparent or reflective than the second portion 114 of target medium 108, and the conditions for detecting the desired portion of target medium 108 may therefore be reversed. The optical sensor package 100 may be designed and calibrated to detect a decrease in opacity (i.e., an increase in transmittance or transparency). For example, the sensor package 100 may indicate a successful detection when the light received at photodiode 104 increases above a detection threshold.

Various embodiments of the present disclosure may include advantages over prior solutions. Conventional optical sensor packages must be screened after manufacture, as packages with too much variation in their manufacture cannot be used for sensitive applications. Optical sensor packages that pass screening must still be manually calibrated for use in a particular environment. By contrast, the optical sensor package of the present application may be easily calibrated to account for variations in manufacture and in the use environment.

Information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

What is claimed is:

1. A method of calibration, comprising:
setting, by a controller, an initial detection threshold of a detector;
gradually increasing a power level of a signal generator, the signal generator being in communication with the detector and the controller, causing a detected power at the detector to exceed the initial detection threshold;
storing in a memory, by the controller, a first power level of the signal generator at which the detected power at the detector exceeds the initial detection threshold; and adjusting, by the controller after the power level of the signal generator reaches the first power level, the initial detection threshold of the detector to an adjusted detection threshold by including from the memory a pre-programmed detection buffer amount within the adjusted detection threshold, wherein the detection buffer amount compensates for a variation affecting an amount of signal received at the detector from the signal generator.

2. The method of claim 1, wherein the detector is a photodetector and the signal generator is a light emitting diode (LED).

3. The method of claim 1, wherein:
adjusting the detection threshold to include the detection buffer amount includes decreasing the detection threshold.

4. The method of claim 1, wherein:
adjusting the detection threshold to include the detection buffer amount includes increasing the detection threshold.

5. The method of claim 1, further comprising, prior to gradually increasing the power level of the signal generator, placing a target medium in a communication path between the signal generator and the detector.

6. The method of claim 1, further comprising:
receiving, at the controller from a user, a detection threshold setting signal including the initial detection threshold as a level of a plurality of discrete levels;
receiving, at the controller from the user, a calibration signal instructing the controller to begin gradually increasing the power level of the signal generator; and
receiving, at the controller from the user, a threshold change signal including the user-programmable amount to adjust the initial detection threshold by.

7. The method of claim 1, further comprising:
after storing the power level of the signal generator at which the detected power at the detector exceeds the initial detection threshold, setting, in the memory, a calibration flag to indicate that calibration has occurred.

8. The method of claim 1, further comprising:
setting, at an analog front end amplifier of the detector prior to increasing the power level, a gain;
applying, by the analog front end amplifier of the detector prior to increasing the power level, the gain to the power level;
if, after gradually increasing the power level of the signal generator to a maximum power level, the initial detection threshold has not been exceeded, increasing the gain at the analog front end amplifier; and
after increasing the gain, gradually increasing, by the signal generator, the power level of the signal generator until the detected power at the detector exceeds the initial detection threshold.

9. A computer program product having a non-transitory computer readable medium tangibly recording computer program logic for calibrating a detector and a signal generator, the computer program product comprising:
code to set an initial detection threshold of the detector;
code to ramp up a power level of the signal generator, the signal generator being in communication with the detector, causing a detected power at the detector to exceed the initial detection threshold;
code to store in a memory a first power level of the signal generator at which the detected power at the detector exceeds the initial detection threshold; and
code to adjust, after the signal generator reaches the first power level, the initial detection threshold of the detector to an adjusted detection threshold by including from the memory a pre-programmed detection buffer amount within the adjusted detection threshold, wherein the detection buffer amount compensates for a variation affecting an amount of signal received at the detector from the signal generator.

10. The computer program product of claim 9 having a non-transitory computer readable medium tangibly recording computer program logic for calibrating a detector and a signal generator, the computer program product further comprising:
code to receive, from a user, a detection threshold setting signal including the initial detection threshold as a level of a plurality of discrete levels;
code to receive, from the user, a calibration signal instructing the computer program product to begin gradually increasing the power level of the signal generator; and
code to receive, from the user, a threshold change signal including the user-programmable amount to adjust the initial detection threshold by.

11. The computer program product of claim 9 having a non-transitory computer readable medium tangibly recording computer program logic for calibrating a detector and a signal generator, the computer program product further comprising:
code to set, at an analog front end amplifier of the detector prior to increasing the power level, a gain;
code to apply, by the analog front end amplifier of the detector prior to increasing the power level, the gain to the power level;
code to increase the gain at the analog front end amplifier if, after gradually increasing the power level of the signal generator to a maximum power level, the initial detection threshold has not been exceeded; and
code to gradually increase, by the signal generator, after increasing the gain, the power level of the signal generator until the detected power at the detector exceeds the initial detection threshold.

12. The computer program product of claim 9 having a non-transitory computer readable medium tangibly recording computer program logic for calibrating a detector and a signal generator, wherein:
the code to adjust the detection threshold to include the detection buffer amount includes code to increase or decrease the detection threshold.

13. A computing device comprising:
a memory containing a non-transitory machine readable medium comprising machine executable code having stored thereon instructions for performing a method of calibrating a sensor and a signal generator;
a processor coupled to the memory, the processor configured to execute the machine executable code to cause the processor to:
set an initial detection threshold of the sensor;
gradually increase a power level of the signal generator, the signal generator being in communication with the sensor, causing a detected power at the sensor to exceed the initial detection threshold;
store in a memory a first power level of the signal generator at which the detected power at the sensor exceeds the initial detection threshold; and
adjust the initial detection threshold, after the signal generator reaches the first power level, of the sensor to an adjusted detection threshold by including from the memory a pre-programmed detection buffer amount within the adjusted detection threshold, wherein the detection buffer amount compensates for a variation affecting an amount of signal received at the detector from the signal generator.

14. The computing device of claim 13, the processor further configured to execute the machine executable code to cause the processor to:
receive, from a user, a detection threshold setting signal including the initial detection threshold as a level of a plurality of discrete levels;
receive, from the user, a calibration signal instructing a computer program product to begin gradually increasing the power level of the signal generator; and
receive, from the user, a threshold change signal including the user-programmable amount to adjust the initial detection threshold by.

15. The computing device of claim 13, the processor further configured to execute the machine executable code to cause the processor to:
set, at an analog front end amplifier of the detector prior to increasing the power level, a gain;
apply, by the analog front end amplifier of the detector prior to increasing the power level, the gain to the power level;
increase the gain at the analog front end amplifier if, after gradually increasing the power level of the signal generator to a maximum power level, the initial detection threshold has not been exceeded; and
gradually increase, by the signal generator, after increasing the gain, the power level of the signal generator until the detected power at the sensor exceeds the initial detection threshold.

16. The computing device of claim 13, wherein the machine executable code to cause the processor to adjust the initial detection threshold to include a detection buffer causes the initial detection threshold to be decreased.

17. The computing device of claim 13, wherein the machine executable code to cause the processor to adjust the initial detection threshold to include a detection buffer causes the initial detection threshold to be increased.

18. The method of claim 1, wherein the variation is an expected variation affecting an amount of signal received at the detector from the signal generator.

19. The method of claim 1, wherein the variation occurs during manufacture or during operation based on a transmissivity, a reflectivity, or a position of an object affecting an amount of signal received at the detector from the signal generator.

* * * * *